(12) United States Patent
Yamada et al.

(10) Patent No.: US 7,241,811 B2
(45) Date of Patent: Jul. 10, 2007

(54) AMIDE COMPOUNDS FOR THE POTENTIATION OF CHOLINERGIC ACTIVITY

(75) Inventors: Akira Yamada, Fujiidera (JP); Satoshi Aoki, Ibaraki (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 11/269,612

(22) Filed: Nov. 9, 2005

(65) Prior Publication Data
US 2006/0058396 A1    Mar. 16, 2006

Related U.S. Application Data

(62) Division of application No. 10/653,977, filed on Sep. 4, 2003, now Pat. No. 7,037,942, which is a division of application No. 10/285,526, filed on Nov. 1, 2002, now Pat. No. 6,664,293, which is a division of application No. 09/926,058, filed as application No. PCT/JP00/00601 on Feb. 3, 2000, now abandoned.

(30) Foreign Application Priority Data
Feb. 26, 1999    (AU)    ..................... PP8912

(51) Int. Cl.
C07C 235/42    (2006.01)
A61K 31/165    (2006.01)

(52) U.S. Cl. ..................... 514/617; 564/161
(58) Field of Classification Search ............ 564/161; 514/617
See application file for complete search history.

(56) References Cited

U.S. PATENT DOCUMENTS

| 2,634,263 A | * | 4/1953 | Steinemann | ............ 534/872 |
| 3,574,841 A | | 4/1971 | Driscoll | |
| 4,797,419 A | | 1/1989 | Moos et al. | |
| 5,071,875 A | | 12/1991 | Horn et al. | |
| 6,057,371 A | | 5/2000 | Glennon | |
| 6,664,293 B2 | | 12/2003 | Yamada et al. | |

FOREIGN PATENT DOCUMENTS

| EP | 0 306 375 | 3/1989 |
| EP | 0 343 961 | 11/1989 |
| EP | 0410358 | * 7/1990 |
| FR | 8 287 | 11/1970 |
| WO | WO 95/18617 | 7/1995 |
| WO | WO 96/21640 | 7/1996 |
| WO | WO 96/24588 | 8/1996 |

OTHER PUBLICATIONS

Patent Abstracts of Japan, JP 06 107544, Apr. 19, 1994.
Patent Abstracts of Japan, JP 06 298732, Oct. 25, 1994.
J. M. Yeung, et al., Eur. J. Med. Chem.—Chim. Ther., vol. 21, No. 3, pp. 181-185, "Synthesis of 3,6-Dihydro-1(2H)-Pyridinyl Derivatives with Hyperglycemic Activity", 1986.
V.C. Agwada, Journal of Chemical and Engineering Data, vol. 29, No. 2, pp. 231-235. Potential Central Nervous System Active Agents. 3.Synthesis of Some Substituted Benzamides and Phenylacetamides, 1984.
P. A. Crooks, "A New Synthesis of 2-Aminoidanes," Chemistry and Industry, Jun. 15, 1974, p. 495.

* cited by examiner

*Primary Examiner*—Zinna N. Davis
(74) *Attorney, Agent, or Firm*—Oblon, Spivak, McClelland, Maier & Neustadt, P.C.

(57) ABSTRACT

Amide compounds of the formula:

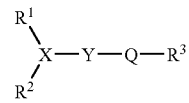

wherein $R^1$ and $R^2$ are taken together to form lower alkenylene, etc.,
$R^3$ is aryl, etc.,
X is N, etc.,
Y is a single bond, etc., and
Q is

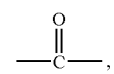

and salt thereof, which are useful as medicament.

12 Claims, No Drawings

AMIDE COMPOUNDS FOR THE POTENTIATION OF CHOLINERGIC ACTIVITY

TECHNICAL FIELD

This invention relates to amide compounds and salts thereof which are useful as a medicament.

BACKGROUND ART

Some aminopiperazine derivatives have been known as useful anti-amnesia or anti-dementia agents, for example, in PCT International Publication Nos. WO 91/01979 and WO 98/35951.

DISCLOSURE OF INVENTION

This invention relates to amide compounds and salts thereof.

More particularly, it relates to amide compounds and salts thereof which have the potentiation of the cholinergic activity, to processes for the preparation thereof, to a pharmaceutical composition comprising the same, and to a method for the treatment and/or prevention of disorders in the central nervous system for mammals, and more particularly to method for the treatment and/or prevention of amnesia, dementia (e.g. senile dementia, Alzheimer's dementia, dementia associated with various diseases such as cerebral vascular dementia, cerebral post-traumatic dementia, dementia due to brain tumor, dementia due to chronic subdural hematoma, dementia due to normal pressure hydrocephalus, post-meningitis dementia, Parkinson's disease type dementia, etc.), and the like. Additionally, the object compound is expected to be useful as therapeutical and/or preventive agents for schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism.

One object of this invention is to provide new and useful amide compounds and salts thereof which possess the potentiation of the cholinergic activity.

Another object of this invention is to provide processes for preparation of the amide compounds and salts thereof.

A further object of this invention is to provide a pharmaceutical composition comprising, as an active ingredient, said amide compounds and salt thereof.

Still further object of this invention is to provide a therapeutic method for the treatment and/or prevention of aforesaid diseases in mammals, using the amide compounds and salts thereof.

The amide compounds of this invention can be represented by the following general formula [I]:

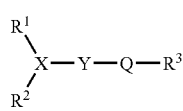

[I]

wherein $R^1$ and $R^2$ are each aryl or ar(lower)alkyl, or are taken together to form lower alkylene or lower alkenylene, each of which may be substituted with aryl or may be condensed with a cyclic hydrocarbon optionally substituted with lower alkyl, lower alkoxy, aryl, aryloxy or halogen, $R^3$ is lower alkyl, lower alkoxy, aryl, arylamino or aryloxy, each of which may be substituted with lower alkoxy or halogen, pyridyl, or pyridylamino, X is CH or N, Y is a single bond or —NH—, and Q is

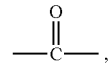

and salts thereof.

The object compound [I] or its salt can be prepared by processes as illustrated in the following reaction schemes.

Process 1

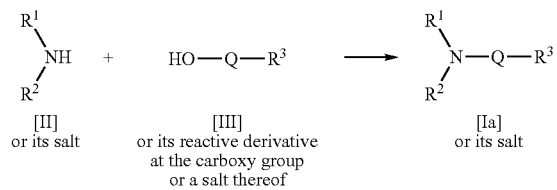

Process 2

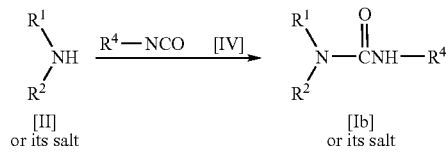

Process 3

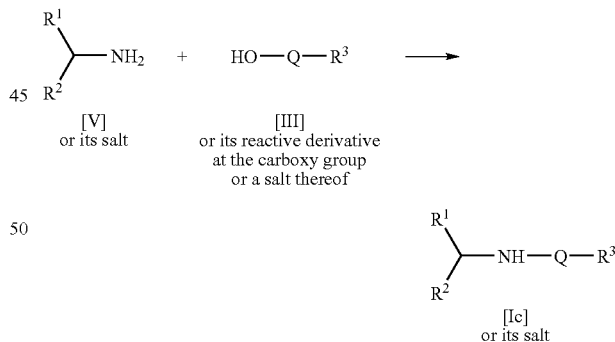

Process 4

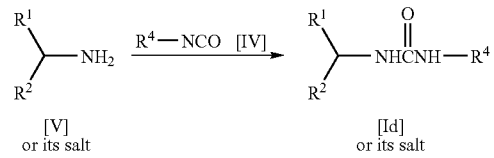

Process 5

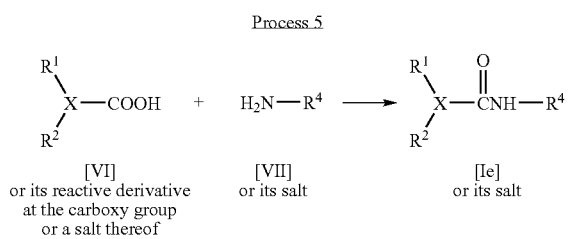

| [VI] | [VII] | [Ie] |
| or its reactive derivative at the carboxy group or a salt thereof | or its salt | or its salt | wherein $R^1$, $R^2$, $R^3$, X and Q are each as defined above, and
$R^4$ is aryl which may be substituted with lower alkoxy or halogen, or pyridyl.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the term "ar(lower)alkyl" may be a straight or branched $C_1$-$C_6$ alkyl such as methyl, ethyl, propyl, isopropyl, butyl, isobutyl, tert-butyl, pentyl, ethylpropyl, hexyl or the like, in which preferable one is methyl.

Suitable "aryl" and aryl or ar moiety in the terms "ar(lower)alkyl", "aryloxy" and "arylamino" may be phenyl, naphthyl, pentyl substituted with lower alkyl [e.g. tolyl, xylyl, mesityl, cumenyl, di(tert-butyl)phenyl, etc.] and the like, in which preferable one is phenyl.

Suitable "halogen" may be fluorine, chlorine, bromine and iodine, in which preferable one is fluorine.

Suitable "ar(lower)alkyl" may be benzyl, phenethyl, phenylpropyl, benzhydryl, trityl and the like, in which preferable one is benzyl.

Suitable "lower alkylene" may be a straight or branched $C_1$-$C_6$ alkylene such as methylene, ethylene, trimethylene, propylene, tetramethylene, pentamethylene, hexamethylene, methylpentamethylene or the like, in which preferable one is tetramethylene or pentamethylene.

Suitable "lower alkenylene" may be a straight or branched $C_2$-$C_6$ alkenylene such as vinylene, propenylene, butenylene, pentenylene, methylpentenylene, hexenylene, pentadienylene or the like, in which preferable one is butenylene, pentenylene or methylpentenylene.

Suitable "lower alkoxy" may be a straight or branched $C_1$-$C_6$ alkoxy such as methoxy, ethoxy, propoxy, isopropoxy, methylpropoxy, butoxy, isobutoxy, tert-butoxy, pentyloxy, hexyloxy or the like, in which preferable one is methoxy.

Suitable "cyclic hydrocarbon" may be a saturated or unsaturated cyclic hydrocarbon such as cyclopentane, cyclohexane, benzene, naphthalene, indan, indene or the like, in which preferable one is benzene.

Preferred compound [I] is one having aryl or ar(lower)alkyl for $R^1$, aryl or ar(lower)alkyl for $R^2$, aryl or arylamino, each of which may be substituted with halogen for $R^3$, CH or N for X, a single bond or —NH— for Y, and

for Q; or one having lower alkenylene which may be substituted with aryl or may be condensed with benzene optionally substituted with lower alkoxy for $R^1$ and $R^2$ to be taken together to form, aryl or arylamino, each of which may be substituted with halogen, pyridyl, or pyridylamino for $R^3$, CH or N for X, a single bond or —NH— for Y, and

Suitable salts of the object compound [I] are pharmaceutically acceptable conventional non-toxic salts and include acid addition salt such as an inorganic acid addition salt [e.g. hydrochloride, hydrobromide, sulfate, phosphate, etc.], an organic acid addition salt [e.g. formate, acetate, trifluoroacetate, maleate, tartrate, methanesulfonate, benzenesulfonate, toluenesulfonate, etc.], a salt with an amino acid [e.g. aspartic acid salt, glutamic acid salt, etc.], a metal salt such as an alkali metal salt [e.g. sodium salt, potassium salt, etc.] and alkaline earth metal salt [e.g. calcium salt, magnesium salt, etc.] and the like.

The processes for preparing the object compound [I] are explained in detail in the following.

Process 1

The compound [Ia] or its salt can be prepared by reacting a compound [II] or its salt with a compound [III] or its reactive derivative at the carboxy group or a salt thereof.

Suitable salts of the compounds [Ia] and [II] may be the same as those exemplified for the compound [I].

Suitable salts of the compound [III] and its reactive derivative at the carboxy group may be metal salt or alkaline earth metal salt as exemplified for the compound [I].

Suitable reactive derivative at the carboxy group or the compound [III] may include an ester, an acid halide, an acid anhydride and the like. The suitable examples of the reactive derivatives may be an acid halide [e.g. acid chloride, acid bromide, etc.];

a symmetrical acid anhydride; a mixed acid anhydride with an acid such as aliphatic carboxylic acid [e.g. acetic acid, pivalic acid, etc.], substituted phosphoric acid [e.g. dialkylphosphoric acid, diphenylphosphoric acid, etc.]; an ester such as substituted or unsubstituted lower alkyl ester [e.g. methyl ester, ethyl ester, propyl ester, hexyl ester, trichloromethyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxyphthalimide or 1-hydroxybenzotriazole, 1-hydroxy-6-chloro-1H-benzotriazole, or the like. These reactive derivatives can be optionally selected according to the kind of the compound [III] to be used.

The reaction is usually carried out in a conventional solvent such as water, acetone, dioxane, chloroform, methylene chloride, ethylene dichloride, tetrahydrofuran, ethyl acetate, N,N-dimethylformamide, pyridine or any other organic solvent which does not adversely influence the reaction. Among these solvents, hydrophilic solvent may be used in a mixture with water.

The reaction is also preferably carried out in the presence of a conventional base such as triethylamine, diisopropylethylamine, pyridine, N,N-dimethylaminopyridine, etc., or a mixture thereof.

When the compound [III] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like.

The reaction temperature is not critical, and the reaction can be carried out under cooling to heating.

Process 2

The compound [Ib] or its salt can be prepared by reacting a compound [II] or its salt with a compound [IV].

Suitable salts of the compounds [Ib] and [II] may be the same as those exemplified for the compound [I].

This reaction is usually carried out in a solvent such as dioxane, tetrahydrofuran, benzene, toluene, chloroform, methylene chloride or any other organic solvent which does not adversely influence the reaction.

The reaction temperature is not critical, and the reaction is usually carried out under cooling to warming.

Process 3

The compound [Ic] or its salt can be prepared by reacting a compound [V] or its salt with a compound [III] or its reactive derivative at the carboxy group or a salt thereof.

Suitable salts of the compounds [Ic] and [V] may be the same as those exemplified for the compound [I].

Suitable salts of the compound [III] and its reactive derivative at the carboxy group may be metal salt or alkaline earth metal salt as exemplified for the compound [I].

This reaction can be carried out in substantially the same manner as Process 1, and therefore the reaction mode and reaction condition [e.g. solvent, reaction temperature, etc.] of this reaction are to be referred to those as explained in Process 1.

Process 4

The compound [Id] or its salt can be prepared by reacting a compound [V] or its salt with a compound [IV].

Suitable salts of the compounds [Id] and [V] may be the same as those exemplified for the compound [I].

This reaction can be carried out in substantially the same manner as Process 2, and therefore the reaction mode and reaction condition [e.g. solvent, reaction temperature, etc.] of this reaction are to be referred to those explained in Process 2.

Process 5

The compound [Ie] or its salt can be prepared by reacting a compound [VI] or its reactive derivative at the carboxy group, or a salt thereof with a compound [VII] or its salt.

Suitable salts of the compounds [Ie], [VI] and its reactive derivative at the carboxy may be the same as those exemplified for the compound [I].

Suitable salt of the compound [VII] may be acid addition salt as exemplified for the compound [I].

This reaction can be carried out in substantially the same manner as Process 1, and therefore the reaction mode and reaction condition [e.g. solvent, reaction temperature, etc.] of this reaction are to be referred to those as explained in Process 1.

The compounds obtained by the above processes can be isolated and purified by a conventional method such as pulverization, recrystallization, column chromatography, reprecipitation, or the like.

It is to be noted that the compound [I] and the other compounds may include one or more stereoisomer(s) such as optical isomer(s) or geometrical isomer(s) due to asymmetric carbon atom(s) and double bond(s), and all of such isomers and mixture thereof are included within the scope of this invention.

Additionally, it is to be noted that any solvate [e.g. enclosure compound (e.g. hydrate, ethanolate, etc.)] of the compound [I] or a salt thereof is also included within the scope of this invention.

The object compound [I] and salts thereof possess strong potentiation of the cholinergic activity, and are useful for the treatment and/or prevention of disorders in the central nervous system for mammals, and more particularly of amnesia, dementia (e.g. senile dementia, Alzheimer's dementia, dementia associated with various diseases such as cerebral vascular dementia, cerebral post-traumatic dementia, dementia due to brain tumor, dementia due to chronic subdural hematoma, dementia due to normal pressure hydrocephalus, post-meningitis dementia, Parkinson's disease type dementia, etc.) and the like. Additionally, the object compound is expected to be useful as therapeutical and/or preventive agents for schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness (narcolepsy), Parkinson's disease or autism.

In order to illustrate the usefulness of the object compound [I], the pharmacological data of the compound [I] is shown in the following.

Test

Penile Erection in Rat (This test was carried out according to a similar manner to that described in Jpn. J. Pharmacol., Vol. 64, 147-153 (1994))

(i) Method

Male Fischer 344 rats at the age of 8 weeks (n=7) were used. All rats were handled 3 minutes a day for three successive days before the tests. The rats were tested in groups of seven and various doses of the test compound were given in semi-randomized order. The test compounds were suspended in 0.5% methyl-cellulose immediately before use, and given intraperitoneally in a volume of 1 ml/kg just before the start of test. Immediately after injection, each rat was placed in a perspex box (25×25×35 cm) and its behavior was observed for 60 minutes, during which time the number of penile erections was counted. A mirror was situated behind each box to facilate of the rat. Data was expressed as a mean number.

(ii) Test Result

| Test Compound (Example No.) | Dose (mg/kg) | Penile Erection (Number/hr) |
|---|---|---|
| 2 | 0.32 | 0.57 |
| 6 | 0.32 | 0.60 |
| 8 | 0.1 | 0.60 |
| 7 | 0.1 | 0.71 |

It is clear that the compound having the above-mentioned activity ameliorates the memory deficits (i.e. amnesia, dementia, etc.) from the description in the Journal of Pharmacology and Experimental Therapeutics, Vo. 279, No. 3, 1157-1173 (1996). Further, it is expected that the compound having the above-mentioned activity is useful as therapeutical and/or preventive agent for aforesaid diseases from some patent applications (e.g. PCT International Publication No. WO 98/27930, etc.).

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral or parenteral administration. The pharmaceutical preparations may be capsules, tablets, dragees, granules, suppositories, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Preparations and Examples are given for the purpose of illustrating this invention.

Preparation 1

To a solution of 4-methylcyclohex-3-enecarbonyl chloride (2 ml) in a mixture of methanol (20 ml) and tetrahydrofuran (20 ml) was added aqueous sodium hydroxide (4N, 20 ml). The resultant mixture was stirred at ambient temperature for 1 hour, and evaporated. The residue was taken up into a mixture of water and ethyl acetate and adjusted pH to around 1. The organic layer was separated, washed with brine, dried over magnesium sulfate, and evaporated under reduced pressure to give 4-methylcyclohex-3-enecarboxylic acid, which was used without further purification.

NMR (DMSO-$d_6$, δ): 1.60 (3H, s), 1.35-1.65 (1H, m), 1.75-2.2 (5H, m), 2.25-2.45 (1H, m), 5.25-5.4 (1H, m), 12.09 (1H, br s) MASS (LD) (m/z): 139.2

Preparation 2

To a solution of 4-methylcyclohex-3-enecarboxylic acid (1.7 g) and triethylamine (1.8 ml) in tert-butanol (35 ml) was added diphenylphospholyl azide (2.6 ml), and the mixture was refluxed for 8 hours. After cooling to ambient temperature, the reaction mixture was diluted with ethyl acetate, washed in turn with hydrochloric acid (1N), aqueous sodium hydrogen carbonate, and brine, and dried over magnesium sulfate. Evaporation under reduced pressure gave a residue, which was chromatographed on silica gel (150 ml) eluting with 1-3% ethyl acetate in n-hexane to give 1-tert-butoxycarbonylamino-4-methylcyclohex-3-ene (0.82 g).

MNR (DMSO-$d_6$, δ): 1.37 (9H, s), 1.60 (3H, s), 1.65-2.2 (6H, m), 3.2-3.4 (1H, m), 5.2-5.3 (1H, m), 6.68 (1H, br s) MASS (LD) (m/z): 234.3

Preparation 3

To a solution of 1-tert-butoxycarbonylamino-4-methylcyclohex-3-ene (0.4 g) in a mixture of anisole (0.4 ml) and dichloromethane (0.8 ml) was added trifluoroacetic acid (1.2 ml) at 0° C. and the mixture was allowed to stir at 0° C. for 1 hour. Evaporation gave a residue, which was taken up into a solution of hydrogen chloride in dioxane (4N, 2 ml). Evaporation under reduced pressure and trituration with diisopropyl ether gave 1-amino-4-methylcyclohex-3-ene hydrochloride, which was used without further purification.

EXAMPLE 1

A solution of 1,2,3,6-tetrahydropyridine (0.25 g) and 4-phenoxycarbonylaminopyridine (0.64 g) in 1,2-dichloroethane (5 ml) was heated to 75° C. for 6 hours. Evaporation of the solvent gave a residue, which was chlomatographed on silica gel (50 ml) eluting with 0-5% methanol in dichloromethane, and taken up into a solution of hydrogen chloride in ethyl acetate (4N, 2 ml). Evaporation under reduced pressure and trituration with diisopropyl ether gave 1-(pyridin-4-ylcarbamoyl)-1,2,3,6-tetrahydropyridine hydrochloride (0.43 g).

MNR (DMSO-$d_6$, δ): 2.05-2.35 (2H, m), 3.64 (2H, t, J=6 Hz), 4.05 (2H, t, J=2.5 Hz), 5.6-5.8 (1H, m), 5.8-6.0 (1H, m), 8.06 (2H, d, J=7 Hz), 8.55 (2H, d, J=7 Hz), 10.58 (1H, s), 14.72 (1H, br s) MASS (LD) (m/z): 204.2

EXAMPLE 2

To a stirred solution of 1,2,3,6-tetrahydropyridine (82 mg) in tetrahydrofuran (2 ml) was added 4-fluorophenyl-isocyanate (0.112 ml) at ambient temperature. After stirring at ambient temperature for 10 hours, the solvent was removed by evaporation under reduced pressure, and the residue was triturated with diisopropyl ether to give 1-(4-fluorophenylcarbamoyl)-1,2,3,6-tetrahydropyridine (117 mg).

MNR (DMSO-$d_6$, δ): 2.0-2.2 (2H, m), 3.51 (2H, t, J=5.7 Hz), 3.85-3.95 (2H, m), 5.65-5.95 (2H, m), 6.95-7.15 (2H, m), 7.35-7.55 (2H, m), 8.47 (1H, s) MASS (LD) (m/z): 243.1

EXAMPLE 3

The following compound was obtained according to a similar manner to that of Example 2.

2-(4-Fluorophenylcarbamoyl)-1,2,3,4-tetrahydro-isoquinoline

MNR (DMSO-$d_6$, δ): 2.85 (2H, t, J=6 Hz), 3.69 (2H, t, J=6 Hz), 4.63 (2H, s), 7.07 (2H, t, J=9 Hz), 7.18 (4H, s), 7.48 (2H, dd, J=5, 9 Hz), 8.60 (1H, s) MASS (LD) (m/z): 293.2

EXAMPLE 4

To a solution of 1-tert-butoxycarbonylamino-4-methylcyclohex-3-ene (0.18 g) in a mixture of anisole (0.18 ml) and dichloromethane (0.36 ml) was added trifluoroacetic acid (0.54 ml) at 0° C. and the mixture was allowed to stir at 0° C. for 1 hour. Evaporation gave a residue, which was taken up into 1,2-dichloroethane (5 ml). To the mixture were added triethylamine (0.6 ml) and 4-phenoxycarbonylaminopyridine (0.183 g), and the resultant mixture was heated to 75° C. for 6 hours. Evaporation gave a residue, which was chromatographed on silica gel (50 ml) eluting with 7% methanol in dichloromethane, and taken up into a solution of hydrogen chloride in ethyl acetate (4N, 2 ml). Evaporation under reduced pressure and trituration with diisopropyl ether gave N-(4-methylcyclohex-3-en-1-yl)-N'-(pyridin-4-yl)urea hydrochloride (0.144 g).

MNR (DMSO-$d_6$, δ): 1.64 (3H, s), 1.4-2.4 (6H, m), 3.6-3.9 (1H, m), 5.2-5.35 (1H, m), 7.26 (1H, d, J=8 Hz), 7.82 (2H, d, J=7 Hz), 8.51 (2H, d, J=7 Hz)., 10.91 (1H, s), 14.50 (1H, br s) MASS (LD) (m/z): 232.2

EXAMPLE 5

To a suspension of 1-amino-4-methylcyclohex-3-ene hydrochloride (0.103 g) in dichloromethane (5 ml) were added in turn pyridine (0.14 ml) and 4-fluorobenzoyl chloride (83 µl) at 0° C. The mixture was allowed to warm to ambient temperature and stirred for 1 hour, which was taken up into a mixture of water and ethyl acetate. The separated organic layer was washed in turn with hydrochloric acid (1N), aqueous sodium hydrogen carbonate, and brine, and dried over magnesium sulfate. Evaporation under reduced pressure gave a residue, which was chromatographed on silica gel (50 ml) eluting with 0-20% ethyl acetate in n-hexane to give 1-(4-fluorobenzoylamino)-4-methylcyclohex-3-ene (98 mg).

MNR (DMSO-$d_6$, δ): 1.59 (3H, s), 1.4-2.3 (6H, m), 3.8-4.1 (1H, m), 5.35-5.5 (1H, m), 7.27 (2H, t, J=9 Hz), 7.89 (2H, dd, J=5, 9 Hz), 8.25 (1H, d, J=7 Hz) MASS (APCI) (m/z): 234

EXAMPLE 6

The following compound was obtained according to a similar manner to that of Example 5.

2-(4-Fluorobenzoylamino)-1,2,3,4-tetrahydronaphthalene

MNR (DMSO-$d_6$, δ): 1.65-1.9 (1H, m), 1.95-2.25 (1H, m), 2.7-3.1 (4H, m), 4.05-4.3 (1H, m), 7.08 (4H, s), 7.2-7.4 (2H, m), 7.85-8.05 (2H, m), 8.45 (1H, d, J=7.5 Hz) MASS (APCI) (m/z): 270

EXAMPLE 7

To a suspension of 1-amino-4-methylcyclohex-3-ene hydrochloride (103 mg) in dichloromethane (5 ml) were added in turn pyridine (0.14 ml), 4-pyridinecarbonyl chloride hydrochloride (0.124 g) and N,N-dimethylaminoyridine (0.11 g) at 0° C. The mixture was allowed to warm to ambient temperature and was allowed to stir for 1 hour. The reaction mixture was taken up into a mixture of water and ethyl acetate, and adjusted pH to 4.6. The separated organic layer was washed in turn with water and brine, and dried over magnesium sulfate. Evaporation under reduced pressure gave a residue, which was triturated with diisopropyl ether to give 1-(pyridin-4-ylcarbonylamino)-4-methylcyclohex-3-ene (46 mg).

MNR (DMSO-$d_6$, δ): 1.64 (3H, s), 1.45-3.35 (6H, m), 3.8-4.1 (1H, m), 5.25-5.45 (1H, m), 7.74 (2H, dd, J=1.6, 4.5 Hz), 8.53 (1H, d, J=7.5 Hz), 8.70 (2H, dd, J=1.6, 4.5 Hz) MASS (APCI) (m/z): 217

EXAMPLE 8

The following compound was obtained according to a similar manner to that of Example 7.

2-(Pyridin-4-ylcarbonylamino)-1,2,3,4-tetrahydronaphthalene

MNR (DMSO-$d_6$, δ): 1.65-1.9 (1H, m), 1.95-2.15 (1H, m), 2.7-3.15 (4H, m), 4.05-4.3 (1H, m), 7.10 (.4H, s), 7.78 (2H, dd, J=1.6, 4.5 Hz), 8.65-8.8 (3H, m) MASS (APCI) (m/z): 253

EXAMPLE 9

1) To a solution of 1-tert-butoxycarbonylamino-4-methylcyclohex-3-ene (0.18 g) in a mixture of anisole (0.18 ml) and dichloromethane (0.36 ml) was added trifluoroacetic acid (0.54 ml) at 0° C. and the mixture was allowed to stir at 0° C. for 1 hour. Evaporation gave a residue containing 1-amino-4-methylcyclohex-3-ene.

2) The residue containing 1-amino-4-methylcyclohex-3-ene was taken up into dichloromethane (5 ml). To the mixture were added triethylamine (0.6 ml) and 4-fluorophenyl-isocyanate (97 µl) at 0° C. and the resultant mixture was allowed to stir for 30 minutes at 0° C. Evaporation under reduced pressure gave a residue, which was taken up into a mixture of water and ethyl acetate. The separated organic layer was washed with brine, evaporated under reduced pressure, and triturated with n-hexane to give N-(4-methylcyclohex-3-en-1-yl)-N'-(4-fluorophenyl)urea (0.206 g).

MNR (DMSO-$d_6$, δ): 1.63 (3H, s), 1.3-1.9 (3H, m), 1.9-2.1 (2H, m), 2.1-2.4 (1H, m), 3.6-3.85 (1H, m), 5.25-5.35 (1H, m), 6.07 (1H, d, J=8 Hz), 7.04 (2H, t, J=9 Hz),7.36 (2H, dd, J=5, 9 Hz), 8.38 (1H, s) MASS (LD) (m/z): 271.2

EXAMPLE 10

The following compound was obtained by using 2-amino-1,2,3,4-tetrahydronaphthalene as a starting compound according to a similar manner to that of Example 2.

N-(4-Fluorophenyl)-N'-(1,2,3,4-tetrahydronaphtalen-2-yl)urea

MNR (DMSO-$d_6$, δ): 1.6-1.8 (1H, m), 1.8-2.05 (1H, m), 2.63 (1H, dd, J=8, 16 Hz), 2.83 (2H, t, J=7 Hz), 3.02 (1H, dd, J=5, 16 Hz), 3.8-4.1 (1H, m), 6.22 (1H, d, J=7.5 Hz), 6.95-7.2 (2H, m), 7.12 (4H, s), 7.3-7.45 (2H, m), 8.40 (1H, s) MASS (APCI) (m/z): 285

EXAMPLE 11

To a solution of aminodiphenylmethane (0.4 g) in dichloromethane (5 ml) were added in turn pyridine (0.21 ml) and 4-fluorobenzoyl chloride (0.23 ml) at 0° C. The mixture was allowed to warm to ambient temperature and stirred for 1 hour, which was taken up into a mixture of water and ethyl acetate. The separated organic layer was washed in turn with hydrochloric acid (1N), aqueous sodium hydrogen carbonate and brine, and dried over magnesium sulfate. Evaporation under reduced pressure gave a residue, which was triturated with diisopropyl ether to give (4-fluorobenzoylamino)-diphenylmethane (0.49 g).

MNR (DMSO-$d_6$, δ): 6.40 (1H, d, J=9 Hz), 7.2-7.45 (12H, m), 8.01 (2H, dd, J=5, 9 Hz), 9.30 (1H, d., J=9 Hz) MASS (APCI) (m/z): 306

EXAMPLE 12

To a solution of 4-fluoroaniline (0.2 g) in dichloromethane (10 ml) were added in turn pyridine (0.19 ml) and diphenylcarbamoyl chloride (0.417 g) at 0° C. The mixture was allowed to warm to ambient temperature and stirred for 10 hours, and to the mixture was added N,N-dimethylaminopyridine (0.22 g), and the mixture was allowed to stir for another 1 hour. The reaction mixture was taken up into a mixture of water and ethyl acetate. The separated organic layer was washed in turn with hydrochloric acid (1N), aqueous sodium hydrogen carbonate and brine, and dried over magnesium sulfate. Evaporation under reduced pressure gave a residue, which was triturated with diisopropyl ether to give N,N-diphenyl-N'-4-fluorophenylurea (0.384 g).

MNR (DMSO-$d_6$, δ): 7.07 (2H, t, J=9 Hz), 7.15-7.3 (6H, m), 7.3-7.5 (6H, m), 8.45 (1H, s) MASS (APCI) (m/z): 307

EXAMPLE 13

To a solution of (R)-1,2,3,4-tetrahydronaphthalen-2-ylamine hydrochloride (0.9 g) in dichloromethane (15 ml) were added in turn triethylamine (1.71 ml) and 4-fluorobenzoyl chloride (0.58 ml) at 0° C. The mixture was allowed to warm to ambient temperature and stirred for 1 hour, which was taken up into a mixture of water and ethyl acetate. The separated organic layer was washed in turn with hydrochloric acid (1N), aqueous sodium hydrogen carbonate and brine, and dried over magnesium sulfate. Evaporation under reduced pressure gave a residue, which was triturated with diisopropyl ether to give (R)-4-fluoro-N-(1,2,3,4-tetrahydronaphthalen-2-yl)benzamide (1.26 g).

MNR (DMSO-$d_6$, δ): 1.60-1.89 (1H, m), 1.95-2.16 (1H, m), 2.70-3.14 (4H, m), 4.05-4.30 (1H, m), 7.09 (4H, s), 7.30 (2H, t, J=8.9 Hz), 7.86-8.04 (2H, m), 8.45 (1H, d, J=7.6 Hz) MASS (APCI) (m/z): 270.3

EXAMPLE 14

To a solution of (S)-1,2,3,4-tetrahydronaphthalen-2-ylamine hydrochloride (0.9 g) in dichloromethane (15 ml) were added in turn triethylamine (1.71 ml) and 4-fluorobenzoyl chloride (0.58 ml) at 0° C. The mixture was allowed to warm to ambient temperature and stirred for 1 hour, which was taken up into a mixture of water and ethyl acetate. The separated organic layer was washed in turn with hydrochloric acid (1N), aqueous sodium hydrogen carbonate and brine, and dried over magnesium sulfate. Evaporation under reduced pressure gave a residue, which was triturated with diisopropyl ether to give (S)-4-fluoro-N-(1,2,3,4-tetrahydronaphthalen-2-yl)benzamide (1.26 g).

MNR (DMSO-$d_6$, δ): 1.60-1.89 (1H, m), 1.95-2.16 (1H, m), 2.70-3.14 (4H, m), 4.05-4.30 (1H, m), 7.09 (4H, s), 7.30 (2H, t, J=8.9 Hz), 7.86-8.04 (2H, m)., 8.45 (1H, d, J=7.6 Hz) MASS (APCI) (m/z): 270.3

EXAMPLE 15

To a solution of 7-methoxy-1,2,3,4-tetrahydronaphthalen-2-ylamine (0.49 g) in dichloromethane (5 ml) were added in turn pyridine (0.29 ml) and 4-fluorobenzoyl chloride (0.33 ml) at 0° C. The mixture was allowed to warm to ambient temperature and stirred for 1 hour, which was taken up into a mixture of water and ethyl acetate. The separated organic layer was washed in turn with hydrochloric acid (1N), aqueous sodium hydrogen carbonate and brine, and dried over magnesium sulfate. Evaporation under reduced pressure gave a residue, which was triturated with diisopropyl ether to give 4-fluoro-N-(7-methoxy-1,2,3,4-tetrahydronaphthalene-2-yl)-benzamide (497 mg).

MNR (DMSO-$d_6$, δ): 1.60-1.85 (1H, m), 1.92-2.13 (1H, m), 2.63-3.10 (4H, m), 3.70 (3H, s), 4.00-4.25 (1H, m), 6.60-6.79 (2H, m), 7.00 (1H, d, J=8.2 Hz), 7.30 (2H, t, J=8.9 Hz), 7.89-8.04 (2H, m), 8.44 (1H, d, J=7.6 Hz) MASS (APCI) (m/z): 300

EXAMPLE 16

To a solution of 6-methoxy-1,2,3,4-tetrahydronaphthalen-2-ylamine (0.57 g) in dichloromethane (5 ml) were added in turn triethylamine (0.46 ml) and 4-fluorobenzoyl chloride (0.30 ml) at 0° C. The mixture was allowed to warm to ambient temperature and stirred for 1 hour, which was taken up into a mixture of water and ethyl acetate. The separated organic layer was washed in turn with hydrochloric acid (1N), aqueous sodium hydrogen carbonate and brine, and dried over magnesium sulfate. Evaporation under reduced pressure gave a residue, which was triturated with diisopropyl ether to give 4-fluoro-N-(6-methoxy-1,2,3,4-tetrahydronaphthalen-2-yl)-benzamide (0.59 g).

MNR (DMSO-$d_6$, δ): 1.60-1.85 (1H, m), 1.92-2.10 (1H, m), 2.60-3.07 (4H, m), 3.71 (3H, s), 4.00-4.30 (1H, m), 6.60-6.75 (2H, m), 6.99 (1H, d, J=8.2 Hz), 7.30 (2H, t, J=8.9 Hz), 7.80-8.04 (2H, m), 8.42 (1H, d, J=7.6 Hz) MASS (APCI) (m/z): 300

EXAMPLE 17

To a solution of indan-2-ylamine (0.297 g) in dichloromethane (5 ml) were added in turn pyridine (0.23 ml) and 4-fluorobenzoyl chloride (0.26 ml) at 0° C. The mixture was allowed to warm to ambient temperature and stirred for 1 hour, which was taken up into a mixture of water and ethyl acetate. The separated organic layer was washed in turn with hydrochloric acid (1N), aqueous sodium hydrogen carbonate and brine, and dried over magnesium sulfate. Evaporation under reduced pressure gave a residue, which was triturated with diisopropyl ether to give 4-fluoro-N-(indan-2-yl)benzamide (0.325 g).

MNR (DMSO-$d_6$, δ): 2.94 (2H, dd, J=6.7, 16.0 Hz), 3.24 (2H, dd, J=6.7, 16.0 Hz), 4.55-4.80 (1H, m), 7.06-7.40 (6H, m), 7.83-8.04 (2H, m), 8.67 (1H, d, J=6.7 Hz) MASS (APCI) (m/z): 256

The invention claimed is:

1. A compound, or a salt thereof, of the formula:

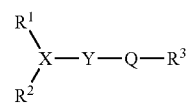

wherein $R^1$ and $R^2$ are taken together to form pentenylene condensed with benzene optionally substituted with lower alkyl, lower alkoxy, phenyl or halogen,
X is CH,
Y is —NH—, and
Q is

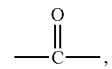

and
$R^3$ is phenyl substituted with halogen, phenylamino substituted with halogen, or pyridyl.

2. The compound according to claim 1, wherein
$R^1$ and $R^2$ are taken together to form pentenylene which is condensed with benzene, and
$R^3$ is phenyl which is substituted with halogen.

3. The compound according to claim 1, which is (R)-4-fluoro-N-(1,2,3,4-tetrahydronaphthalen-2-yl)benzamide.

4. A process for preparing a compound of claim 1, or a salt thereof, of the formula:

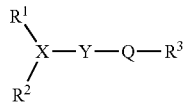
[V]

wherein $R^1$, $R^2$, $R^3$, Q, X and Y are defined in claim 1; said process comprising:

reacting a compound of the formula:

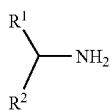
[V]

or its salt with a compound of the formula:

HO-Q-$R^3$   [III]

or its reactive derivative at the carboxy group, or a salt thereof to provide a compound of the formula:

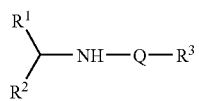
[Ic]

or its salt, in the above formulas, wherein $R^1$, $R^2$, $R^3$ and Q are each as defined in claim 1.

5. A pharmaceutical composition comprising the compound of claim 1, as an active ingredient, in association with a pharmaceutically acceptable, substantially non-toxic carrier or excipient.

6. A method for manufacturing a medicament comprising admixing the compound of claim 1 with a pharmaceutically acceptable carrier or excipient.

7. A solvate or enclosure compound of the compound of claim 1.

8. A method for the treatment of amnesia, dementia, senile dementia, Alzheimer's dementia, dementia associated with various diseases, cerebral vascular dementia, cerebral post-traumatic dementia, dementia due to brain tumor, dementia due to chronic subdural hematoma, dementia due to normal pressure hydrocephalus, post-meningitis dementia, Parkinson's disease type dementia, schizophrenia, depression, stroke, head injury, nicotine withdrawal, spinal cord injury, anxiety, pollakiuria, incontinence of urine, myotonic dystrophy, attention deficit hyperactivity disorder, excessive daytime sleepiness, narcolepsy, Parkinson's disease, or autism, comprising administering an effective amount of the compound of claim 1 to a subject in need thereof.

9. The method of claim 8, wherein said effective amount ranges from 0.1 mg/body to 1,000 mg/body.

10. A method for the treatment of schizophrenia which comprises administering an effective amount of the compound of claim 1 to a subject in need thereof.

11. A method for the treatment of amnesia which comprises administering an effective amount of the compound of claim 1 to a subject in need thereof.

12. A method for the treatment of dementia, senile dementia or Alzheimer's dementia which comprises administering an effective amount of the compound of claim 1 to a subject in need thereof.

* * * * *